(12) United States Patent
Ridden et al.

(10) Patent No.: US 11,484,512 B2
(45) Date of Patent: Nov. 1, 2022

(54) NANOPARTICLES FORMED OF A POLYMER AND TERBINAFINE

(71) Applicant: Blueberry Therapeutics Limited, Macclesfield (GB)

(72) Inventors: John Ridden, Macclesfield (GB); Christine Caroline Ridden, Macclesfield (GB); David Cook, Macclesfield (GB); Julie Cook, Macclesfield (GB)

(73) Assignee: Blueberry Therapeutics Limited, Macclesfield (GB)

( * ) Notice: Subject to any disclaimer, the term of this patent is extended or adjusted under 35 U.S.C. 154(b) by 308 days.

(21) Appl. No.: 16/627,460

(22) PCT Filed: Jun. 28, 2018

(86) PCT No.: PCT/GB2018/051802
§ 371 (c)(1),
(2) Date: Dec. 30, 2019

(87) PCT Pub. No.: WO2019/002862
PCT Pub. Date: Jan. 3, 2019

(65) Prior Publication Data
US 2020/0155482 A1    May 21, 2020

(30) Foreign Application Priority Data

Jun. 30, 2017 (GB) .................................. 1710491

(51) Int. Cl.
*A61K 31/135*   (2006.01)
*A61P 31/10*    (2006.01)
*A61K 9/00*     (2006.01)
*A61K 9/14*     (2006.01)

(52) U.S. Cl.
CPC .......... *A61K 31/135* (2013.01); *A61K 9/0014* (2013.01); *A61K 9/14* (2013.01); *A61P 31/10* (2018.01)

(58) Field of Classification Search
CPC .................................................. A61K 31/135
See application file for complete search history.

(56) References Cited

U.S. PATENT DOCUMENTS

| 2016/0206567 A1 | 7/2016 | Ridden et al. |
| 2018/0193281 A1* | 7/2018 | Ridden ................ A61K 9/7084 |

FOREIGN PATENT DOCUMENTS

| WO | 2011/073395 | * | 6/2011 | ............ A61K 47/18 |
| WO | WO-2011/073395 A1 | | 6/2011 | |
| WO | WO-2015/044669 | | 2/2015 | |
| WO | WO-2017/006112 A1 | | 1/2017 | |
| WO | WO-2017/163091 A1 | | 9/2017 | |

OTHER PUBLICATIONS

Baraldi et al., Human Nail Plate Modifications Induced by Onychomycosis: Implications for Topical Therapy, Pharmaceutical Research, Vo. 32(5):1626-33, May 2015.
Elewski et al., Efficacy, safety and tolerability of topical terbinafine nail solution in patients with mild-to-moderate toenail onychomycosis: results from three randomized studies using double-blind vehicle-controlled and open-label active-controlled designs, Journal of the European Academy of Dermatology and Venereology, vol. 27(3):287-294, Mar. 2013.
Foster et al., Epidemiologic Surveillance of Cutaneous Fungal Infection in the United States from 1999 to 2002, Journal of the American Academy of Dermatology, vol. 50(5):748-752, May 2004.
Halmy et al., Experience with Nail Lacquers Containing Amorolfine 5% and Ciclopirox 8% in Patients with Onychomycosis, Journal of the American Academy of Dermatology, vol. 52(3):126, Mar. 2005.
Leyden, Pharmacokinetics and Pharmacology of Terbinafine and Itraconazole, Journal of the American Academy of Dermatology, vol. 38(5 Pt 3):S42-7, May 1998.
Scher et al., Onychomycosis: Diagnosis and Definition of Cure, Journal of the American Academy of Dermatology, vol. 56(6):939-944, Jun. 2007.
International Search Report and Written Opinion issued on International Patent Application No. PCT/GB2018/051802 dated Dec. 5, 2018.

* cited by examiner

*Primary Examiner* — Paul V Ward
(74) *Attorney, Agent, or Firm* — Howson & Howson LLP

(57) ABSTRACT

The present invention relates to a composition for use in the treatment of onychomycosis and/or tinea pedis, the composition comprising a polymer capable of forming nanoparticles and terbinafine, or derivative or salt thereof, wherein the nanoparticles are formed with and/or in the presence of terbinafine, or derivative or salt thereof and wherein the composition is administered topically to provide a daily dose to an infected area in the range of about 5 μg to about 50 μg of terbinafine. The invention also relates to a combination of the composition and a liquid dispensing device for dispensing a pre-defined quantity of the composition to a user's toes and/or inter-digital spaces and/or front of the foot.

18 Claims, 8 Drawing Sheets

Figure 9
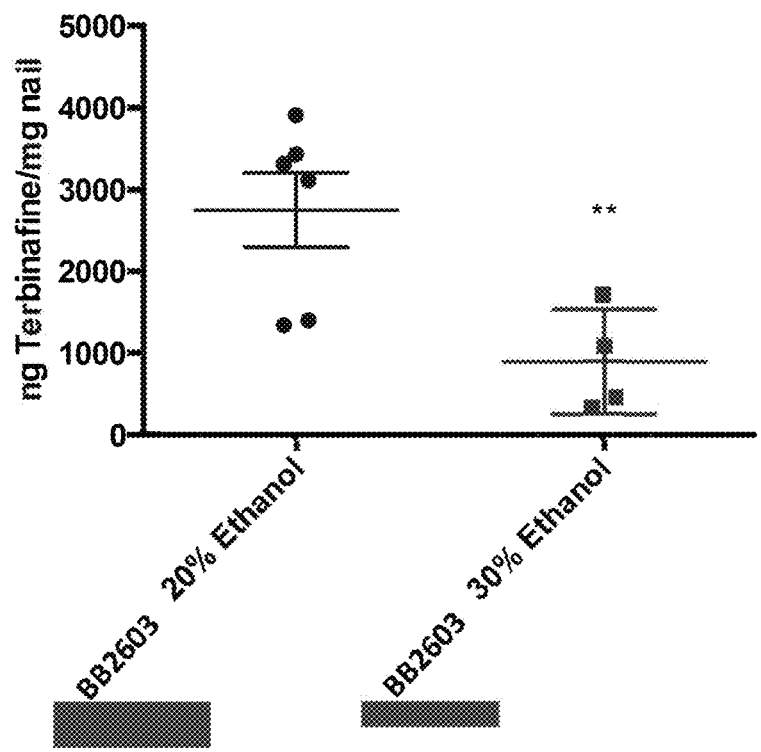
| Figure 10A | Figure 10B | Figure 10C | Figure 10D | Figure 10E |
|---|---|---|---|---|
| 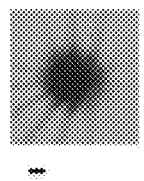 | 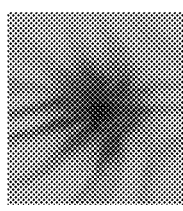 | 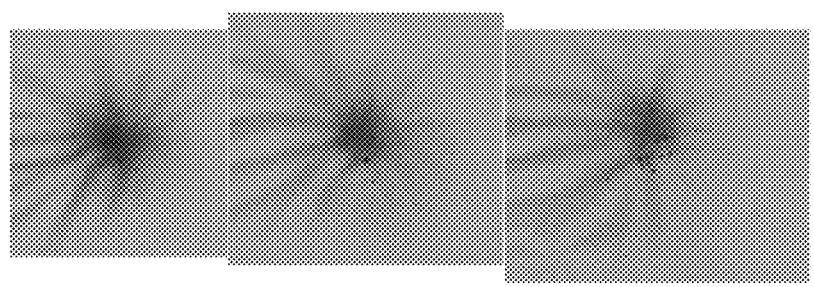 | 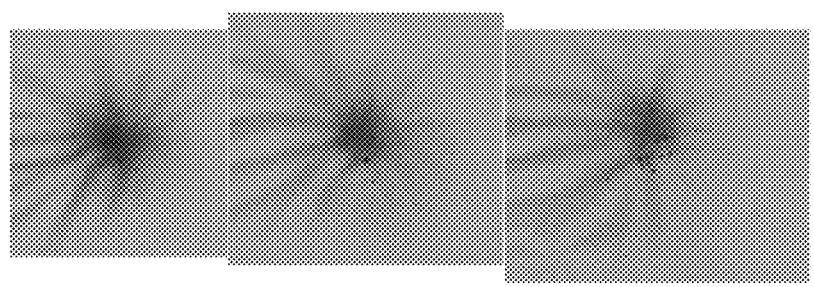 | 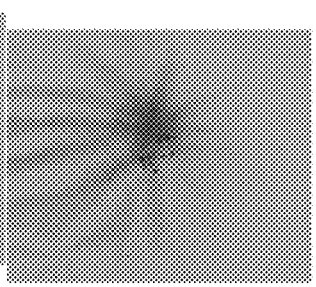 |
| 5cm | 10cm | 15cm | 20cm | 25cm |

Foot template

Underlying paper

NANOPARTICLES FORMED OF A POLYMER AND TERBINAFINE

CROSS-REFERENCE TO RELATED APPLICATIONS

This is a National Stage Entry under 35 U.S.C. 371 of International Patent Application No. PCT/GB2018/051802, filed Jun. 28, 2018, which claims priority to Great Britain Patent Application No. 1710491.0, filed Jun. 30, 2017. These applications are incorporated by reference herein.

TECHNICAL FIELD OF THE INVENTION

The invention relates to compositions (and methods of producing such compositions) comprising nanoparticles formed of a polymer and terbinafine. Such compositions are particularly suited, but not limited, to the treatment of fungal nail and/or skin infections.

BACKGROUND TO THE INVENTION

Fungal infections are increasingly common in both human and animals, yet the treatment of such infections remains problematic due to toxicity of the antifungal compositions, poor solubility of these compositions and the remote location of some infections which can prove difficult to reach using traditional medicinal formulations.

A broad spectrum of antifungals such as amphotericin B, hamycin, filipin and nystatin were discovered in 1960s. But due to toxicity only hamycin and nystatin are used topically and amphotericin B systemically. A breakthrough in antifungal therapy was the introduction of azoles especially ketoconazole. The major classes of antifungals currently used are polyenes, azoles allyl amines, lipopeptides, and pyrimidines. However, polyenes are toxic to mammalian cells. Azoles are well tolerated topically but have side effects when given systemically and there have been several reports of resistance to azoles. Flucytosin is the most common pyrimidine used. Whilst it has excellent tissue penetration, resistance against flucytosine can develop rapidly and produce gastro intestinal side effects. Lipopetides display low toxicity and several trials are still on going to test efficacy.

The development of new antifungals is constrained because fungi are eukaryotic and cellular targets, if disrupted, can also damage host cells. The increase in fungal infections and increase in use of antifungals has resulted in emergence of resistance among fungi. Anti-fungal resistance has high clinical impact as fungal diseases are causing an increase in morbidity and mortality of immunocompromised patients.

It is estimated that around 40% of newly discovered drugs fail due to lack of proper delivery because of aqueous solubility problems. In the case of topical delivery of drugs, the barrier properties of skin often require permeation enhancers to achieve the required dose of drugs.

Onychomycosis (more commonly known as fungal nail infection) causes nails to thicken, discolor, disfigure, and split. Without treatment, the nails can become so thick that they press against the inside of shoes, causing pressure, irritation, and pain. There are risks for further complications especially in patients with diabetes, those with peripheral vascular disease and the immunocompromised patient. Fungal nail infection may cause psychological and social problems. The incidence of fungal nail infection increases with age and has a prevalence of ~30% of the over 60s with significant incidence in Europe with even higher levels in Asia. Fungal nail infection may affect one or more toenails and/or fingernails and can completely destroy the nail if left untreated.

The current treatment for fungal nail infection is as topical nail lacquer/paint (such as amorolfine) 1-2 times per week for 6-12 months and/or oral antifungals (such as terbinafine or itraconazole). Oral antifungals can have severe side effects such as gastro-intestinal upset and can even result in liver failure. Relapse is commonly reported in 25-50% of cases and many patients will not commit to the treatment course due to predicted side effects and length of treatment time and often only when disease becomes more aggressive will treatment begin. Current oral or topical treatments can take 6-12 months to work. Oral treatments have to saturate the systemic circulation to reach the toes and the increased doses increases the risk to the gastro-intestinal and liver complications. Topical treatments are ineffective at penetrating the thickened nail and again require high dosing.

Athlete's Foot (otherwise known as ringworm of the foot, Tinea pedis or moccasin foot) is a fungal infection of the skin generally caused by fungi in the genus *Trichophyton* (most commonly *T. rubrum* or *T. mentagrophytes*). The various parasitic fungi that cause athlete's foot also can cause other skin infection such as onychomycosis and Tinea cruris. Whilst distinct from fungal nail infection, athlete's foot also has issue with compliance and duration of treatment.

WO2015/044669 discloses a topical composition (and methods of producing such compositions) for the treatment of a fungal infection comprising a polymer capable of forming nanoparticles and an antifungal agent. WO2017/006112 discloses antifungal compositions comprising nanoparticles formed of a polymer and terbinafine, wherein the nanoparticles comprise particles in the range of 0.5 to 5 nm and/or in the range of 150 to 250 nm.

An object of the present invention is to address one or more of the above problems associated with current antifungal treatments. One object of the present invention is to provide a topical anti-fungal treatment. Another object of the present invention is to provide a treatment which allows for better penetration of an anti-fungal agent through the nail and/or dermis. It is desirable if the present invention could be used as a single treatment for addressing both onychomycosis and tinea pedis and also be easily applied resulting in a high treatment adherence and have a low re-occurrence rate.

SUMMARY OF THE INVENTION

In accordance with the present invention, there is provided a composition for use in the treatment of onychomycosis and/or tinea pedis, the composition comprising a polymer capable of forming nanoparticles and terbinafine, or derivative or salt thereof, wherein the nanoparticles are formed with and/or in the presence of terbinafine, or derivative or salt thereof and wherein the composition is administered topically to provide a daily dose to an infected area in the range of about 5 µg to about 50 µg of terbinafine.

In accordance with a further alternative first aspect of the present invention, there is provided a composition for use as a medicament, for use in the treatment of onychomycosis and/or tinea pedis, the composition comprising a polymer capable of forming nanoparticles and terbinafine, or derivative or salt thereof, wherein the nanoparticles are formed with and/or in the presence of terbinafine, or derivative or salt thereof and wherein the composition is administered topically to provide a daily dose to an infected area in the range of about 5 μg to about 50 μg of terbinafine.

In accordance with a yet further alternative first aspect of the present invention, there is provided use of composition for the treatment of onychomycosis and/or tinea pedis, the composition comprising a polymer capable of forming nanoparticles and terbinafine, or derivative or salt thereof, wherein the nanoparticles are formed with and/or in the presence of terbinafine, or derivative or salt thereof and wherein the composition is administered topically to provide a daily dose to an infected area in the range of about 5 μg to about 50 μg of terbinafine.

In accordance with yet another further alternative first aspect of the present invention, there is provided use of a composition for the manufacture of a medicament for the treatment of onychomycosis and/or tinea pedis, the composition comprising a polymer capable of forming nanoparticles and terbinafine, or derivative or salt thereof, wherein the nanoparticles are formed with and/or in the presence of terbinafine, or derivative or salt thereof and wherein the composition is administered topically to provide a daily dose to an infected area in the range of about 5 μg to about 50 μg of terbinafine.

In accordance with yet another further alternative first aspect of the present invention, there is provided a method of treating onychomycosis and/or tinea pedis, by topically administering to a patient in need thereof, a composition comprising a polymer capable of forming nanoparticles and terbinafine, or derivative or salt thereof, wherein the nanoparticles are formed with and/or in the presence of terbinafine, or derivative or salt thereof and wherein the composition is administered in a daily dose to an infected area in the range of about 5 μg to about 50 μg of terbinafine.

Preferably, the daily dose to a infected area of terbinafine is in the range of about 10 μg to about 40 μg. More preferably, the daily dose to an infected area of terbinafine is in the range of about 15 μg to about 35 μg. More preferably, the daily dose to an infected area of terbinafine is in the range of about 20 μg to about 30 μg. Even more preferably, the daily dose to an infected area of terbinafine is in the range of about 20 μg to about 30 μg. Most preferably, the daily dose to an infected area of terbinafine is about 25 μg.

The term "daily dose" is intended to mean the quantity of terbinafine which is topically applied to an infected area of the digits and/or the inter-digital spaces and/or front of the foot, hand or limb of an individual or animal suffering from onychomycosis and/or tinea pedis. It is envisaged that more than one area of the individual or animal may be infected and therefore require separate doses of the composition.

The daily dose will preferably take place in the morning after the affected area has been washed or soaked and dried. Preferably, the affected area is not washed or soaked again for up to about 8 hours. The daily dose may take place in the morning or the evening.

The composition may be administered by means of a spray. In order to obtain substantially complete coverage the digits and/or the inter-digital spaces and/or front of the foot or hand or infected limb of a patient suffering from onychomycosis and/or tinea pedis, for the purposes of calculating the daily dose, it has been estimated that approximately 50% of the spray of the composition will be applied to the patient and approximately 50% of the spray of the composition will be wasted and will coat the floor or surface upon which the affect limb is resting. Therefore, whilst it is most preferred that the daily dose of terbinafine is about 25 μg, when applying the composition to the infected area, the total dose contained in the sprayed dose will be twice that of the desired dose so as to account for approximately 50% wastage. It therefore follows that preferably, when the composition is administered by means of a spray, the quantity of terbinafine which is sprayed towards the infected area is the range of about 20 μg to about 80 μg. More preferably, when the composition is administered by means of a spray, the quantity of terbinafine which is sprayed towards the infected area is the range of about 30 μg to about 70 μg. Even more preferably, when the composition is administered by means of a spray, the quantity of terbinafine which is sprayed towards the infected area is the range of about 40 μg to about 60 μg. Most preferably, when the composition is administered by means of a spray, the quantity of terbinafine which is sprayed towards the infected area is about 50 μg.

The composition may be administered by means of a spray application. The daily dose may be administered using one or more spray applications. The daily dose may comprise up to about 10 spray applications. Alternatively, the daily dose may comprise up to about 8 spray applications. Preferably, the daily dose may comprise up to about 7 spray applications. Most preferably, the daily dose comprises up to about 5 spray applications. Multiple dose applications, rather than a single dose application, advantageously have been shown to increase the area of coverage when administered by a spray device.

The spray should be effective to cover the entire infected area, digits and/or the inter-digital spaces and/or front of the foot, hand or limb so as to be able to treat onychomycosis and/or tinea pedis.

The composition may comprise:
a) a ratio of terbinafine, or derivative or salt thereof, to polymer in the range of about 1:2 to about 1:4; and
b) up to about 30% (v/v) alcohol.

The polymer may comprise one or more of polyhexamethylene biguanide (PHMB), polyhexamethylene monoguanide (PHMG), polyethylene biguanide (PEB), polytetramethylene biguanide (PTMB) or polyethylene hexamethylene biguanide (PEHMB).

Thus, the polymer may comprise homogeneous or heterogeneous mixtures of one or more of polyhexamethylene biguanide (PHMB), polyhexamethylene monoguanide (PHMG), polyethylene biguanide (PEB), polytetramethylene biguanide (PTMB), polyethylene hexamethylene biguanide (PEHMB), polymethylene biguanides (PMB), poly (allylbiguanidnio-co-allylamine), poly(N-vinylbiguanide), polyallybiguanide.

The most preferred polymer comprises polyhexamethylene biguanide (PHMB).

The term "terbinafine, or derivative or salt thereof" is intended to mean the pharmaceutically active substance related to terbinafine hydrochloride, which is a synthetic allylamine antifungal originally marketed under the trade name Lamisil®. The term is also intended to include pharmaceutical variations, derivatives, alternative salts, of terbinafine hydrochloride such as non-toxic organic, or inorganic, acid, or base, addition salt, in a pharmaceutically acceptable form.

The terbinafine, or derivative or salt thereof, may be present in a formulation in an amount in the range of about 5 to about 1000 μg/ml. Preferably, the terbinafine, or derivative or salt thereof, may be present in a formulation in the range of about 5 to about 600 μg/ml. More preferably, the terbinafine, or derivative or salt thereof, will be present in a formulation in the range of about 25 to about 200 μg/ml. Even more preferably, the terbinafine, or derivative or salt thereof, will be present in a formulation in the range of about 50 to about 150 μg/ml. Most preferably, the terbinafine, or derivative or salt thereof, will be present in a formulation at about 100 μg/ml.

The polymer may be present in a formulation in an amount in the range of about 15 to about 3000 μg/ml. Preferably, the polymer is present in a formulation in the range of about 15 to about 1800 μg/ml. More preferably, the polymer will be present in a formulation in the range of about 75 to about 600 μg/ml. Even more preferably, the polymer will be present in a formulation in the range of about 150 to about 450 μg/ml. Most preferably, the polymer will be present in a formulation at about 300 μg/ml. The polymer will preferably comprise PHMB.

The alcohol may be present in a formulation in an amount in the range of about 5% to about 29% or to about 30% (v/v). More preferably, the alcohol will be in a formulation in an amount in the range of about 10% to about 29% or to about 30% (v/v). Even more preferably, the alcohol will be in a formulation in an amount in the range of about 20% to about 29% or to about 30% (v/v). Yet more preferably, the alcohol will be in a formulation in an amount up to about 25% or 23% (v/v). Most preferably, the alcohol is in a formulation in an amount up to about 20% (v/v).

The alcohol will preferably comprise ethanol, although it may comprise (whether alone or in combination with) other alcohols such as methanol or propanol.

The composition may also comprise water. The water will preferably be distilled water. The water may be present in an amount in a formulation in the range of about 70% to about 95% (v/v). Preferably, the water will be in a formulation in an amount in the range of about 70% to about 90% (v/v). More preferably, the water will be in a formulation in an amount in the range of about 70% to about 80% (v/v). Yet more preferably, the water will be in a formulation in an amount over about 77% (v/v). Most preferably, the water is in a formulation in an amount up to about 90% (v/v), up to about 80% (v/v) or up to about 79.6% (v/v).

The terbinafine, or derivative or salt thereof, may be present in an amount in the range of about 0.005% w/w to about 1.0% w/w. Preferably, the terbinafine, or derivative or salt thereof, may be present in the range of about 0.005% w/w to about 0.6% w/w. More preferably, the terbinafine, or derivative or salt thereof, will be present in the range of about 0.025% w/w to about 0.2% w/w. Even more preferably, the terbinafine, or derivative or salt thereof, will be present in the range of about 0.05% w/w to about 0.15% w/w. Most preferably, the terbinafine, or derivative or salt thereof, will be present at about 0.1% w/w.

The polymer may be present in an amount in the range of about 0.15% w/w to about 3% w/w. Preferably, the polymer is present in the range of about 0.15% w/w to about 1.8% w/w. More preferably, the polymer will be present in the range of about 0.75% w/w to about 0.6% w/w. Even more preferably, the polymer will be present in the range of about 0.15% w/w to about 0.45% w/w. Most preferably, the polymer will be present at about 0.3% w/w. The polymer will preferably comprise PHMB.

The alcohol may be present in an amount in the range of about 5% w/w to about 29% w/w. Preferably, the alcohol will be in an amount in the range of about 10% w/w to about 29% w/w. More preferably, the alcohol will be in an amount in the range of about 20% w/w to about 29% w/w. Yet more preferably, the alcohol will be in an amount up to about 29% w/w, more preferably up to about 25%, even more preferably up to about 23% w/w and most preferably, the alcohol is in an amount up to about 20% w/w.

The alcohol will preferably comprise ethanol, although it may comprise (whether alone or in combination with) other alcohols such as methanol or propanol.

The composition may also comprise water. The water will preferably be distilled water. The water may be present in an amount in the range of about 70% w/w to about 95% w/w. Preferably, the water will be in an amount in the range of about 70% w/w about 90% w/w. More preferably, the water will be in an amount in the range of about 70% w/w to about 80% w/w. Yet more preferably, the water will be in an amount up to about 70% w/w, more preferably up to about 77% w/w. Most preferably, the alcohol is in an amount up to about 90% w/w, up to about 80% w/w or up to 79.6% w/w.

Preferably, the composition comprises;
(a) terbinafine, or derivative or salt thereof, present in an amount in the range of about 0.005% w/w to about 1% w/w;
(b) a polymer capable of forming nanoparticles and terbinafine, or derivative or salt thereof, wherein the nanoparticles are formed with and/or in the presence of terbinafine, or derivative or salt thereof and wherein the polymer is present in an amount in the range of about 0.015% w/w to about 3% w/w;
(c) alcohol at less than about 30% w/w; and
(d) water at up to about 90% w/w.
More preferably, the composition comprises:
(a) terbinafine, or derivative or salt thereof, present in an amount in the range of about 0.025% w/w to about 0.2% w/w;
(b) polymer present in an amount in the range of about 0.75% w/w to about 0.6% w/w;
(c) alcohol present in an amount in the range of about 20% w/w to about 29% w/w; and
(d) water present in an amount in the range of about 70% w/w about 90% w/w.
Even more preferably, the composition comprises:
(a) terbinafine, or derivative or salt thereof, at about 0.1% w/w;
(b) polymer at about 0.3% w/w;
(c) alcohol at about 20% w/w; and
(d) water at up to about 79.6% w/w.

The ratio of terbinafine, or derivative or salt thereof, to polymer may be about 1:3±0.75. Preferably, the ratio of terbinafine, or derivative or salt thereof, to polymer will be about 1:3±0.5. More preferably, the ratio of terbinafine, or derivative or salt thereof, to polymer will be about 1:3±0.25. Even more preferably, the ratio of terbinafine, or derivative or salt thereof, to polymer will be about 1:3±0.1. Most preferably, the ratio of terbinafine, or derivative or salt thereof, to polymer will be about 1:3.

The nanoparticles may comprise particles formed in two diametrically distinct species. This may comprise a first species in the range of 0.5 to 5 nm and a second species in the range of 50 to 350 nm.

The relative quantities of first species to the second species may be generally equal with one another, or one species may be the more prominent species within the composition.

Preferably, the particles in the first species are in the range of 0.5 to 3 nm. More preferably, the particles in the first species are in the range of 0.5 to 2.5 nm. Most preferably, the particles in the first species are in the range of 0.5 to 2 nm. Preferably, the particles in the second species are in the range of 75 to 325 nm. More preferably, the particles in the second species are in the range of 100 to 300 nm. Most preferably, the particles in the second species are in the range of 150 to 200 nm or 215 nm.

Preferably, the average size of the particles in the first species will be in the range of 0.5 to 1.5 nm. More preferably, the average size of the particles in the first species will be in the range of 0.6 to 1.4 nm. Even more preferably, the average size of the particles in the first species will be in the range of 0.7 to 1.2 nm. Most preferably, the average size of the particles in the first species will be in the region of about 0.9 nm.

Preferably, the average size of the second species of particles will be in the range of 50 to 350 nm. More preferably, the average size of the second species of particles will be in the range of 100 to 300 nm. Even more preferably, the average size of the second species of particles will be in the range of 150 to 200 nm. Most preferably, the average size of the second species of particles will be in the region of about 160 to about 176 nm.

Preferably, the average modal size of the second species of particles will be in the range of 150 to 225 nm. More preferably, the average modal size of the second species of particles will be in the range of 155 to 220 nm. Even more preferably, the average modal size of the second species of particles will be in the range of 160 to 215 nm. Most preferably, the average modal size of the second species of particles will be in the region of about 164 to about 211 nm.

It will be apparent to the skilled addressee that the composition may further comprise one or more of the following components: buffers, excipients, binders, oils, solvents, water, emulsifiers, glycerin, antioxidants, preservatives and fragrances or any additional components usually found in medicaments, and in particular topical creams and ointments. Furthermore, the composition could be in a number of forms such as a paste or a suspension. Alternatively, and more preferably, the composition is substantially free of other components.

A number of techniques may be employed to further process the mixture so as to select the nanoparticles in the required size ranges, such as centrifugation, electrophoretic, chromatographic or filtration methods. The measurement of the size/diameter of the nanoparticles is preferably conducted using dynamic light scattering analysis.

In an additional aspect of the present invention there is provided a spray device for the topical delivery of a composition as herein described above.

In a further aspect of the present invention there is provided a method for topical administration of a composition as herein described above by using a spray device such as a pump dispenser. The composition may be sprayed from the pump dispenser at a distance of about 0 to 30 cm from a target area. Preferably the composition may be sprayed from the pump dispenser at a distance of about 5 to 25 cm from a target area. Most preferably the composition may be sprayed from the pump dispenser at a distance of about 5 to 15 cm from a target area. Advantageously a spray distance of between 5 to 15 cm has been shown to provide full coverage of a target area and less than 50% loss of the sprayed dose to a surrounding area.

In accordance with another aspect of the present invention, there is provided a combination of a composition as herein above described and a liquid dispensing device for dispensing a pre-defined quantity of the composition to an infected area (such as their digits, and/or inter-digital spaces and/or front of their toes and/or hands or infected limb, the device comprising a vessel containing the composition, a nozzle for expelling the composition from the vessel and a pump action mechanism operable by the user to draw the pre-defined quantity of composition from the vessel and expel it via the nozzle, thereby atomizing the composition onto the infected area.

The device may further comprise a metering valve, through which the pre-defined quantity of composition is dispensed. It is preferred that the pre-defined quantity of composition comprises up to about 200 pl. More preferred, the pre-defined quantity of composition comprises up to about 150 μl. Most preferred, the pre-defined quantity of composition comprises up to about 100 μl or about 100 μl.

The device may further comprise and/or be associated with a distance indicator or measurement device to indicate the correct distance the user should place the nozzle of the device relative to the infected area (such as their digits and/or inter-digital spaces and/or front of the foot or hand or limb).

In use, when the nozzle of the device is placed in the range of about 5 cm to 15 cm of the toes and/or inter-digital spaces and/or front of the foot, the nozzle of the device can dispense all of the required dose with up to about 5 pumps. Preferably, in use, when the nozzle of the device is placed about 10 cm of the infected area (such as their digits and/or inter-digital spaces and/or front of the foot or hand or limb), the nozzle of the device can dispense all of the required dose in about 5 pumps.

DETAILED DESCRIPTION OF THE INVENTION

Embodiments of the present invention will now be described, by way of example only, with reference to the following experiments and accompanying figures, in which:

FIG. 1 is a graph showing the results of the nail soak experiments with BB2603 (terbinafine and PHMB nanoparticles) and terbinafine alone where 3mm human nail discs from healthy nail clippings were suspended in BB2603 and terbinafine solutions at equivalent concentrations of active ingredient (0.1, 1 and 10 mg/ml). Washed, dried nails were dissolved in 5M NaOH and the levels of terbinafine determined by quantitative LC-MS/MS;

FIG. 2A is a photograph of a cryosectioned histological sample of a nail clipping from a healthy human volunteer which was soaked for 24 hours at 32° C. in a solution of 0.25 mg/ml PHMB, 0.05 mg/ml FITC labelled PHMB (1 in 5 spike of fluorescently labelled PHMB) and 0.1 mg/ml terbinafine (scale bar is approximately 100 μm);

FIG. 2B is a photograph of a cryosectioned histological sample of a nail clipping from a healthy human volunteer which was soaked in a similar manner to FIG. 2A. Two images are presented of the whole nail section (left hand side scale bar is approximately 100 μm) and the central region of the nail alone (right hand side scale bar is approximately 20 μm). Staining is clearly seen around the margin of the nail that penetrates at least 20 μm into the nail structure itself;

FIG. 3 is a scatter plot graph showing the penetration of terbinafine through healthy human nail samples treated with BB2603 (terbinafine and PHMB nanoparticles) or terbinafine solutions. The concentration of terbinafine was determined by LC-MS/MS in ethanol washes from healthy human nails treated with BB2603 or 0.1 mg/ml terbinafine solutions. Individual samples are plotted. (Diamond shape marker) All terbinafine samples (n=4) were below the limit of detection (<0.1 ng/ml). The two sample sets were compared using a student's unpaired parametric T-test by assuming that the concentrations of terbinafine passing through the nails treated with terbinafine solutions was 0.1 ng/ml (the limit of LC-MS/MS detection). The p-value for this test was 0.04;

FIG. 4 is a scatter plot graph showing levels of terbinafine associated with nails treated with BB2603 (terbinafine and PHMB nanoparticles) or terbinafine solutions. The concentration of terbinafine was determined by LC-MS in dissolved nails samples from healthy human nails treated with BB2603 or 0.1 mg/ml terbinafine solutions. Individual samples are plotted. The two sample sets were compared using a student's unpaired parametric T-test. The p-value for this test was 0.02;

Figures 6A, 6B, 6C, 6D, 6E:
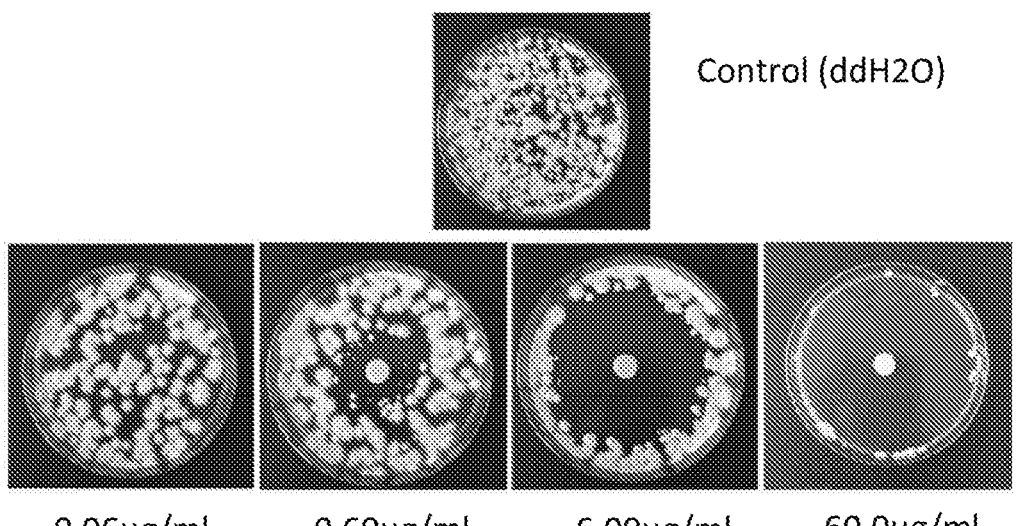
Figure 7A:
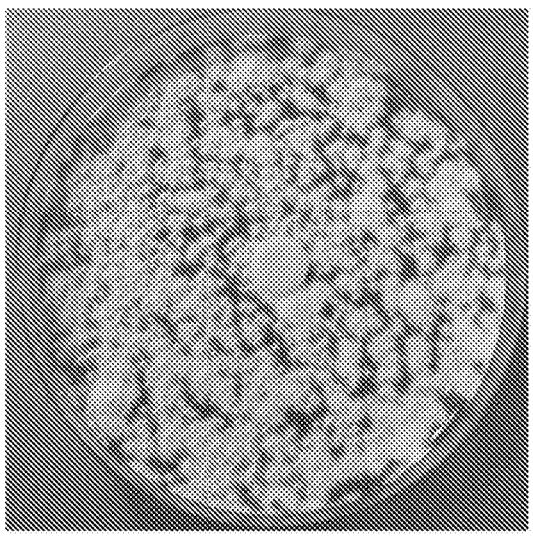
Figure 7B:
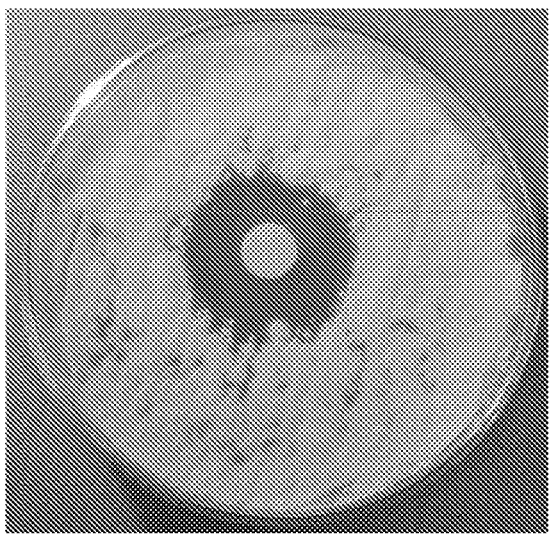
Figure 8:
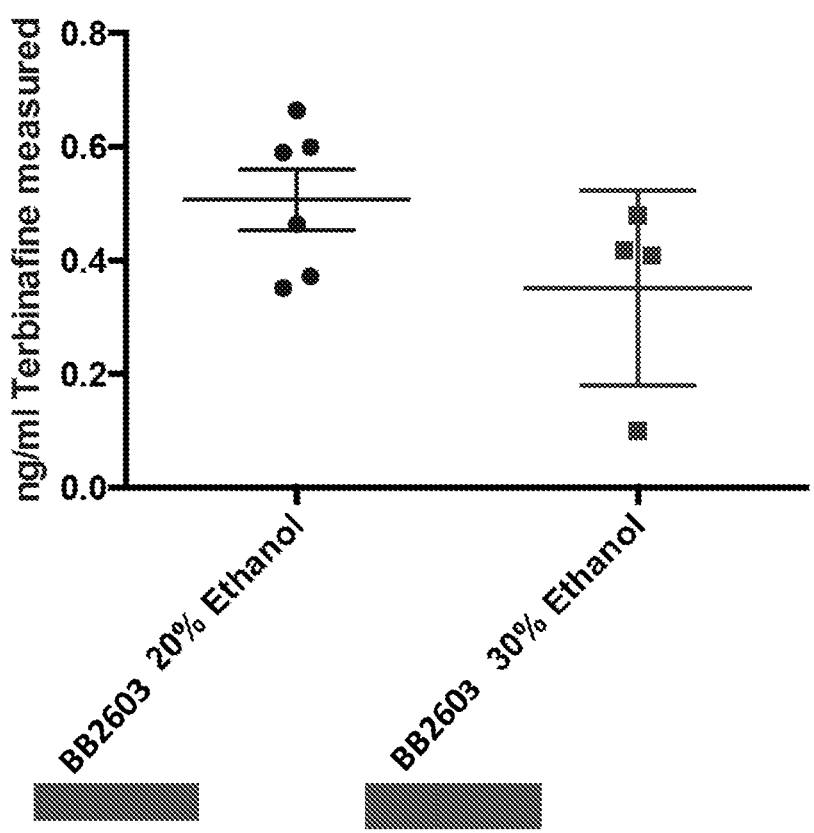
Figure 11:
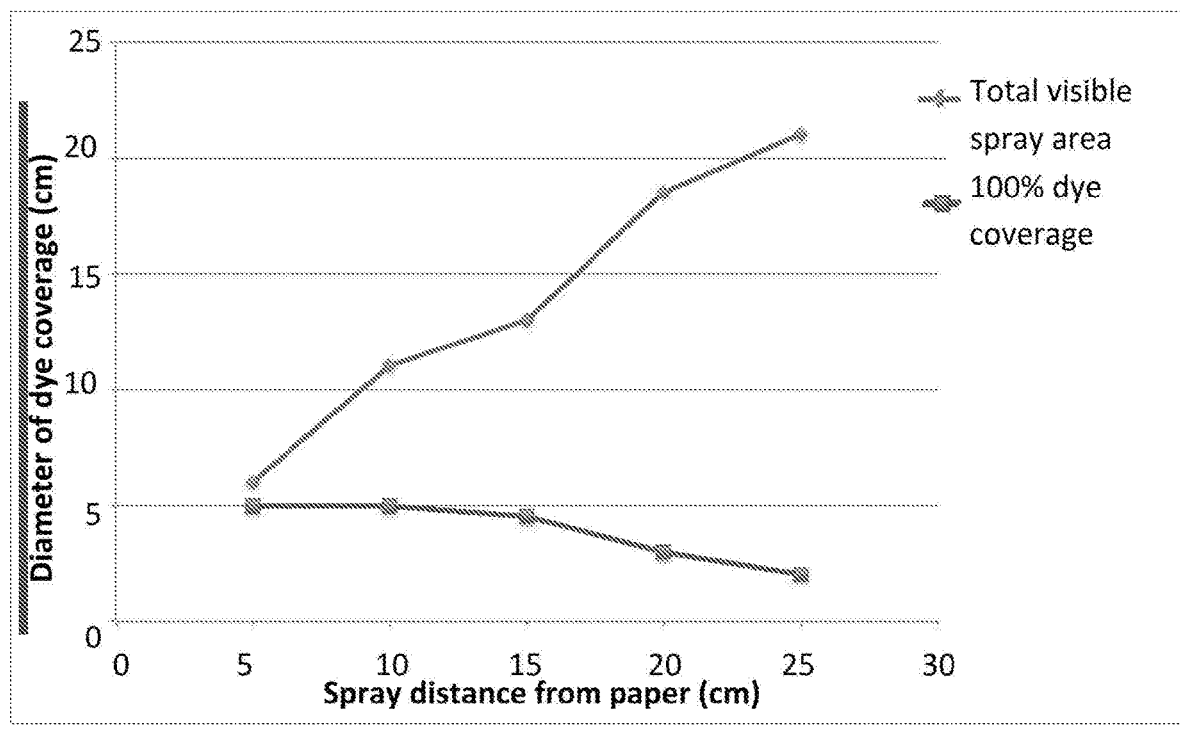
Figure 12:
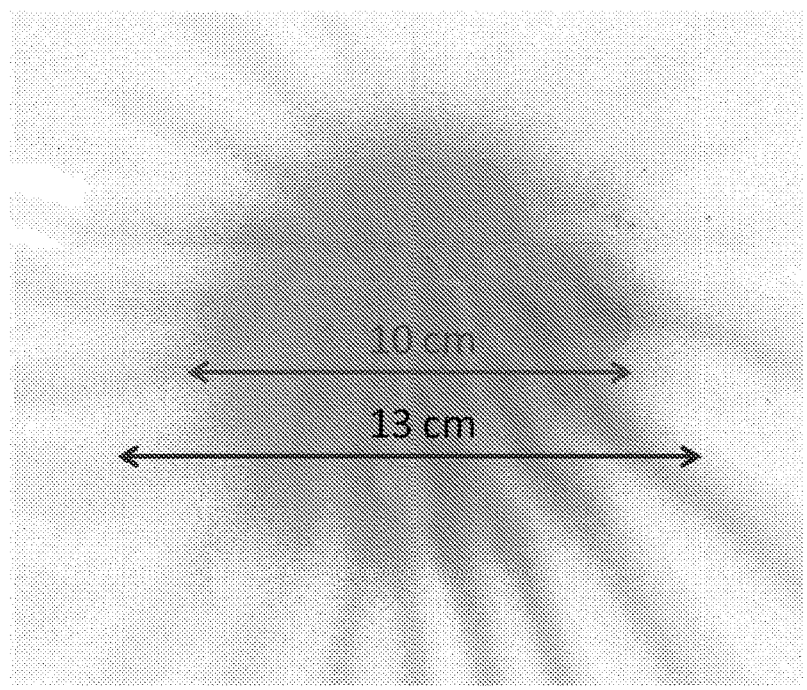
Figure 13A:
Figure 13B:
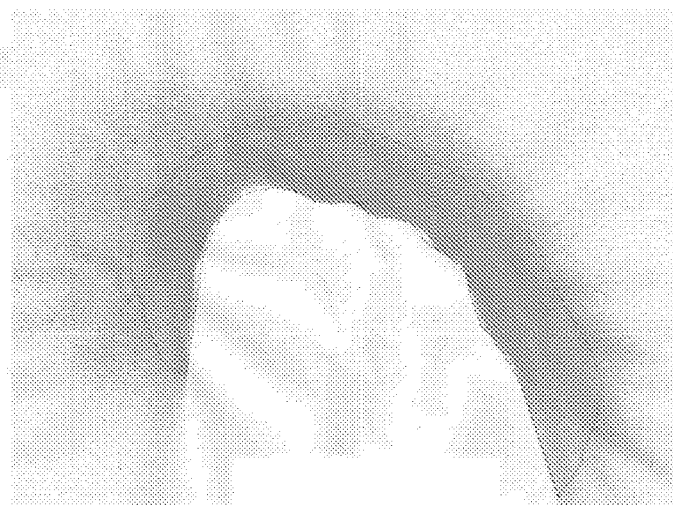

FIGS. 6A-6E are photographic images of yeast extract peptone dextrose (YEPD) agar plates with *Trychophyton mentagrophytes* after incubation for 4 days at 30° C. Each plate had a 10 mm sterile paper disc placed in the centre of the *T. mentagrophytes* lawn. 40 µl of double distilled water or terbinafine solution of varying concentration was spotted onto each paper disc. The concentration of the terbinafine solutions used were: 0 µg/ml (control, FIG. 6A), 0.06 µg/ml (FIG. 6B), 0.6 µg/ml (FIG. 6C), 6.00 µg/ml (FIG. 6D) and 60.0 µg/ml (FIG. 6E);

FIGS. 7A and 7B are photographic images of YEPD plates assessing the efficacy of BB2603 (terbinafine and PHMB nanoparticles) and terbinafine samples passing through healthy human nail against *Trychophyton mentagrophytes* A lawn of *Trychophyton mentagrophytes* was spread onto YEPD agar plates supplemented with 50 µg/ml chloramphenicol. The aqueous samples from the Franz cell collection chamber following 7 days treatment of healthy human nails with either 0.1 mg/ml terbinafine (FIG. 7A) or BB2603 (FIG. 7B) were spotted onto 10 mm paper discs. The discs were placed in the middle of the *Trychophyton* plates, which were then incubated at 30° C. for 5 days to allow the fungi to grow. Antifungal activity of terbinafine from the BB2603 treated nails is seen as a zone of clearance around the disc;

FIG. 8 is a scatter plot graph showing terbinafine concentrations in ethanol washes from nails treated with multiple doses of BB2603 (terbinafine and PHMB nanoparticles). The concentration of terbinafine (determined by LC-MS/MS) in ethanol washes from healthy human nails treated with multiple small doses of BB2603 was either 20% (v/v) ethanol (left hand side) or 30% (v/v) ethanol (right hand side);

FIG. 9 is a scatter plot graph showing terbinafine concentrations in the dissolved nails from nails treated with multiple doses of BB2603 (terbinafine and PHMB nanoparticles). The concentration of terbinafine (determined by LC-MS/MS) in dissolved nails from healthy human nails treated with multiple small doses of BB2603 was either 20% (v/v) ethanol (left hand side) or 30% (v/v) ethanol (right hand side);

FIGS. 10A-10E are images of blue food colouring spots from spot spray tests wherein spraying was conducted at a distance of 5 cm (FIG. 10A), 10 cm (FIG. 10B), 15 cm (FIG. 100), 20 cm (FIG. 10D) and 25 cm (10E) from a sheet of paper. The images are all to the same scale. The scale bar is 1 cm;

FIG. 11 is a line graph showing the diameter of the total area of visible dye coverage (n=2) from the spot spray tests and the diameter of an area showing 100% dye coverage plotted against the distance of the spray from a sheet of paper;

FIG. 12 is an image of a spot from a spot spray test with blue food colouring performed by spraying at a distance of 10 cm from a sheet of paper and conducting 5 repeat spray pumps. The image is not to scale. The diameter of total visible coverage and 100% coverage were measured and are shown on the image;

FIGS. 13A and 13B are images of a foot template (FIG. 13A) and underlying paper (FIG. 17B) treated with 5 dye sprays from a distance of 10 cm. The areas of 100% dye coverage are indicated by a line on both images. The areas if paper corresponding to 100% dye coverage were cut out and the paper weighed as a way of assessing the relative areas of coverage.

The aim of the following experiments was to investigate the potential, efficacy and dosing of a formulation comprising terbinafine and the cationic polymer Polyhexamethylene Biguanide (PHMB) for use in the treatment of onychomycosis and/or tinea pedis.

Nanoparticle Formation with Terbinafine and PHMB

Experiments were initially conducted to form nanoparticles of terbinafine and PHMB. These terbinafine and PHMB nanoparticles were denoted BB2603 throughout the initial experiments.

The BB2603 nanoparticles were initially formed through the combination of terbinafine.HCl with PHMB in 30% (v/v) ethanol to final terbinafine concentrations equivalent to 0.1 mg/ml, 1 mg/ml or 10 mg/ml. Nanoparticle formation was routinely confirmed on Nanosight LM10 Zetasizer instruments (Malvern Instruments). Control terbinafine solutions were made by dissolving terbinafine.HCL in 30% (v/v) ethanol to final concentrations of 0.1 mg/ml, 1 mg/ml or 10 mg/ml.

Initial formulations of terbinafine with PHMB in 30% ethanol were shown to significantly increase the number of nanoparticles formed and resulted in the formation of more mono-disperse nanoparticles than the particles formed with terbinafine alone in 30% ethanol. The results showed that PHMB could be used to form mono-disperse nanoparticles with an antifungal agent which could then be used in the preparation of a topical medicament for the subsequent treatment of a range of potential fungal infections.

Analysis of Nanoparticles

In a solution of BB2603 at an equivalent concentration of 0.1 mg/ml terbinafine, a large number (typically between $5-10\times10^8$ nanoparticles/ml) of monodispersed particles with diameters in the range of 170-210 nm were observed. Higher concentrations of BB2603 (equivalent concentrations of terbinafine of 1 and 10 mg/ml respectively) were also produced for use in initial nail soak experiments (as described below) but these showed a loss of monodispersity, thought to be due to the higher polymer concentration allowing the formation of larger nanoparticle aggregates (data not shown).

Finally the long-term stability of a solution of BB2603 in 30% (v/v) ethanol was assessed by measuring the nanoparticles in solution over a period of 170 days. Analysis was performed using a Nanosight LM10 and so only considered the larger diameter population of BB2603 nanoparticles.

This analysis demonstrated that, despite an initial modest reduction in the number of particles in solution and some variation in the modal size of the particles, BB2603 nanoparticles were essentially stable for at least 5 months at room temperature under ambient light conditions.

Nail Soak Experiments

Samples of healthy human nail were pre-incubated at 30° C. in ddH$_2$O for 2 hours. 3 mm discs were then cut from the clippings using a 3 mm biopsy punch. The nail discs were placed in 250 µl of test solutions in a 1.5 ml tube and incubated at 24 hours at 32° C. in a humidified incubator at 0.5% (v/v) CO$_2$ Nail samples were removed and washed in a large volume of ddH$_2$O to remove any drug solution on the nail. The nails were dried using a clean tissue and then weighed. The weighed nails were dissolved in 200 µl of 5M NaOH at 37° C. for 1 hour. After being dissolved, 200 µl of methanol was added to the samples to ensure that any terbinafine in the samples remained in solution. The amount of terbinafine in dissolved nail sample solutions were analysed using quantitative LC-MS/MS mass spectrometry.

Quantitative mass spectrometry (MS) was used to detect and quantify terbinafine in samples. Sample identifiers were blinded prior to submission for analysis. Analyses used high performance liquid chromatography with tandem mass spectrometry (LC-MS/MS) using a Waters Acquity I-Class UPLC chromatography system coupled with a Waters Xevo TQ-S Mass Spectrometer. Levels of terbinafine were quantified against drug standards on a standard curve from 0.1-10 ng/ml terbinafine. Samples were appropriately diluted to ensure they fell within the standard curve. Samples below 0.1 ng/ml terbinafine were below the limit of detection for this analysis. Concentrations of terbinafine in the nail samples were normalised to the total amount of nail and expressed as ng terbinafine/mg of nail.

Initial research focused on using simple nail "soak" experiments in which 3 mm discs of human nail were incubated in different formulations and test solutions. These experiments were only able to detect whether terbinafine was associating with nail and did not give direct evidence of nail penetration. However they were technically simple to perform, relatively high-throughput and enabled a range of different formulations to be assessed.

Terbinafine in simple solutions of terbinafine was shown to associate with human nail samples. The amount of terbinafine associated with the nail was concentration dependent between 0.1 mg and 1 mg/ml but did not show any further enhancement at a higher concentration of 10 mg/ml. This would indicate that above 1 mg/ml the nail disc has reached an upper limit for the amount of terbinafine that can associate with it.

At an equivalent concentration to 0.1 mg/ml terbinafine no significant difference between BB2603 and a solution of terbinafine was seen, and both produced equivalent concentrations of drug in the dissolved nail samples. As had been observed for terbinafine, there was also an increase in drug association between BB2603 at terbinafine concentrations equivalent to 0.1 and 1 mg/ml but no further increase at 10 mg/ml. Again suggesting that above 1 mg/ml, BB2603 had reached the limit of the amount of drug that can soak into the nail disc in 24 hours. However, compared to terbinafine treated nails, the maximum amount of drug that can associate with nails treated with BB2603 was much higher (1.3-2.5×). This increase was not due to differences in the accessible test surface or overall nail material as all the test were performed on 3 mm nail discs with essentially the same surface area and had weights that only varied by <10% between samples. These experiments therefore suggested that BB2603 increases the maximum amount of terbinafine that can associate with human nail, which indicated that the formulation is enhancing drug delivery into the tissue.

Although the nail soak experiments suggested that BB2603 enhanced drug delivery into nails, they were unable to distinguish between increased drug penetration into the nail and increased drug binding to the nail. It was therefore decided to advance the 0.1 mg/ml BB2603 formulation into histology studies in order to try and obtain direct evidence of nanoparticle penetration into the tissue. This concentration was chosen because it produced the most robust and consistent nanoparticle formulation and, as discussed previously, higher concentrations of BB2603 were much more variable in forming nanoparticles.

Histology Studies

Formulations of BB2603 were made at an equivalent concentration of 0.1 mg/ml terbinafine that included a 1% (w/w) "spike" of FITC conjugated Nanocin™ (a nanoparticle based delivery platform, consisting of PHMB, marketed by Tecrea Ltd, The London Bioscience Innovation Center, 2 Royal College Street, London, NW1 0NH, UK). The labelled BB2603 was used in a nail soak experiment as described above. The washed and dried nails were then sent for histology analyses. Histology and fluorescence microscopy was carried out on frozen cryosections of nail.

Example images from histology studies with FITC labelled BB2603 are shown in FIGS. 6A and 6B. Strong fluorescence was observed around the margins of the nails, consistent with BB2603 binding to the surface of the nail. In addition, we also observed staining penetrating into the nail from the surface. The level of staining varied but we were able to detect fluorescence deep within the nail structure itself (as shown in FIG. 6A in particular).

Although this data is highly suggestive that BB2603 nanoparticles are penetrating into human nail the possibility that the staining observed was only due to free FITC-Nanocin™ needed to be eliminated. It was therefore decided to progress from these histology experiments to using Franz cells and directly measure drug transit across human nail samples.

Franz Cells Nail Penetration Studies

Nail clippings were soaked in water overnight at 30° C. and dried briefly. A 3 mm diameter punch was used to take disc biopsies of the nail clippings. Each nail disc was added to a Franz cell and an upper chamber of the cell attached. 40 µl of the following formulations was added to the upper chambers: 0.3 mg/ml PHMB+0.1 mg/ml terbinafine; or 10 mg/ml terbinafine. Lower collection chambers of the Franz cells were filled with water (approximately 600 µl) and the hole in the base of the sample chamber also filled with ddH$_2$O to prevent bubbles forming beneath the nail. The upper sample chamber was carefully placed into the collection chamber ensuring not to introduce any air bubbles. Excess liquid from the collection chamber was expelled at this point leaving a final volume of liquid in the lower chamber of 500 µl. Parafilm® was used to wrap the join between the upper and lower chambers to prevent liquid evaporation.

For single dose (continuous exposure) experiments, 40 µl of the relevant test sample (BB2603 or terbinafine control) was added into the upper sample chamber using a fine pipette tip, ensuring not to introduce any air bubbles at the nail/liquid interface. The upper chamber was sealed to limit evaporation. For the multiple dose experiments, 5 µl of sample was added every day for 7 days into the upper sample chamber directly onto the nail using a fine pipette tip, ensuring that no air bubbles were introduced at the nail/ liquid interface. The chamber was left open to allow the sample to evaporate. Franz cells were incubated at 32° C. in a humidified incubator at 0.5% (v/v) $CO_2$.

Following incubation of the Franz cell, the sample chamber and collar assembly were carefully removed and all of the liquid taken from the lower collection chamber and hole in the base of the collar. The sample chamber and collar assembly was inverted and the undersides of the nails were then gently washed with 5×20 μl of ethanol to remove any drug associated with the underside of the nail. The combined ethanol washes were retained for analysis (100 μl total volume). This wash was intended to capture any terbinafine that might have passed through the nail. Terbinafine found in either the lower collection chamber or ethanol washes of the underside of the nails represented drug that had passed through the nail.

The nail discs from the Franz cell were also analysed for the presence of terbinafine as follows: the remaining test sample was removed from the upper sample chamber and discarded and the sample chamber washed 5 times with 100 μl dd$H_2O$, with each wash being discarded, in order to remove any residual test solution remaining in the sample chamber. The sample chamber and collar were then disassembled and the nail samples removed. The nails were washed by immersion in a large volume of dd$H_2O$, dried using a clean tissue and weighed. The weighed nails were then dissolved in 200 μl of 5M NaOH at 37° C. for 1 hour. After being dissolved, 200 μl of methanol was added to the samples to ensure that any terbinafine in the samples remained in solution.

FIGS. 3-5B summarise the data from Franz cell analyses of drug transit across human nails samples. Only the data present from the dissolved nail samples and ethanol washes of the underside of the nail are provided as these observations proved to be the most robust between samples. However, it was always possible to detected terbinafine in the lower chamber of nails treated with BB2603, sometimes to very high levels (>0.6 μg/ml). It is believed that this analysis represents a conservative view of the amount of terbinafine passing through the nail in BB2603 treated samples.

Single Dose (Constant Exposure) Experiments

40 μl of solutions of BB2603 (equivalent to 0.1 mg/ml terbinafine) or terbinafine (0.1 mg/ml) in 30% (v/v) ethanol were added to the sample chamber of Franz cells containing healthy human nail samples. The cells were then incubated at 32° C. for 7 days. The samples remained in contact with the upper nail surface for the duration of each experiment. After 7 days, samples from the underside of the nail (ethanol washes) were collected and analysed by LC-MS/MS. Nail samples on day 7 were washed and dissolved using 5M NaOH as described earlier. All the samples collected were analysed for the presence of terbinafine using high performance liquid chromatography with tandem mass spectrometry (LC-MS/MS) on a Waters Acquity I-Class UPLC chromatography system coupled with a Waters Xevo TQ-S Mass Spectrometer. Levels of terbinafine were quantified against drug standards. The limit of detection in these analyses was 0.1 ng/ml.

Figure 1:
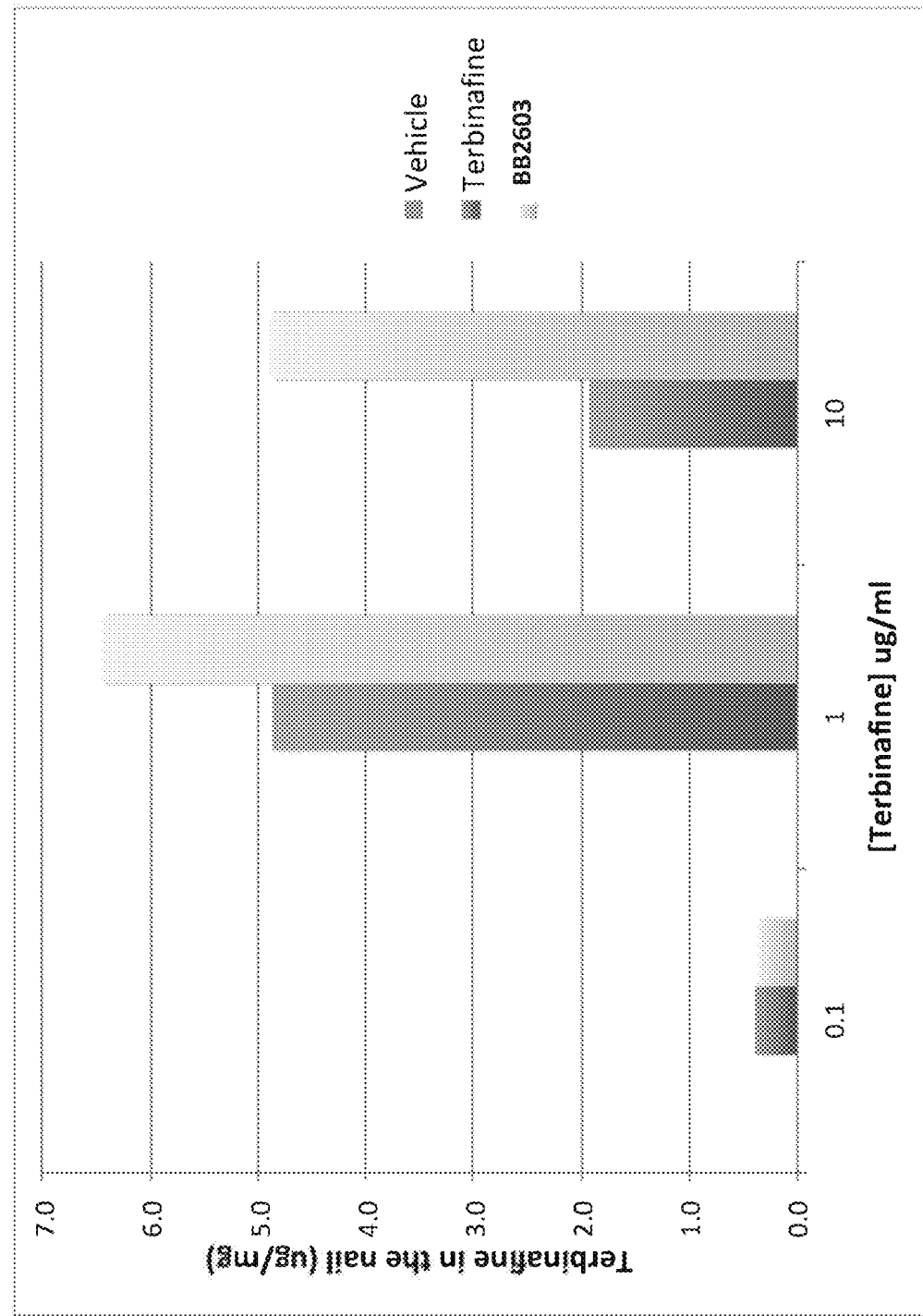
Figure 2B:
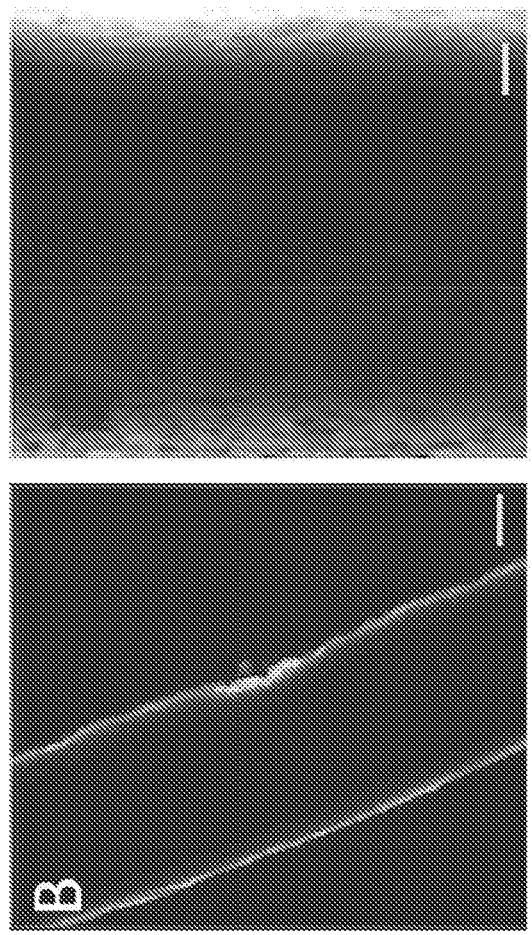
Figure 2A:
Figure 3:
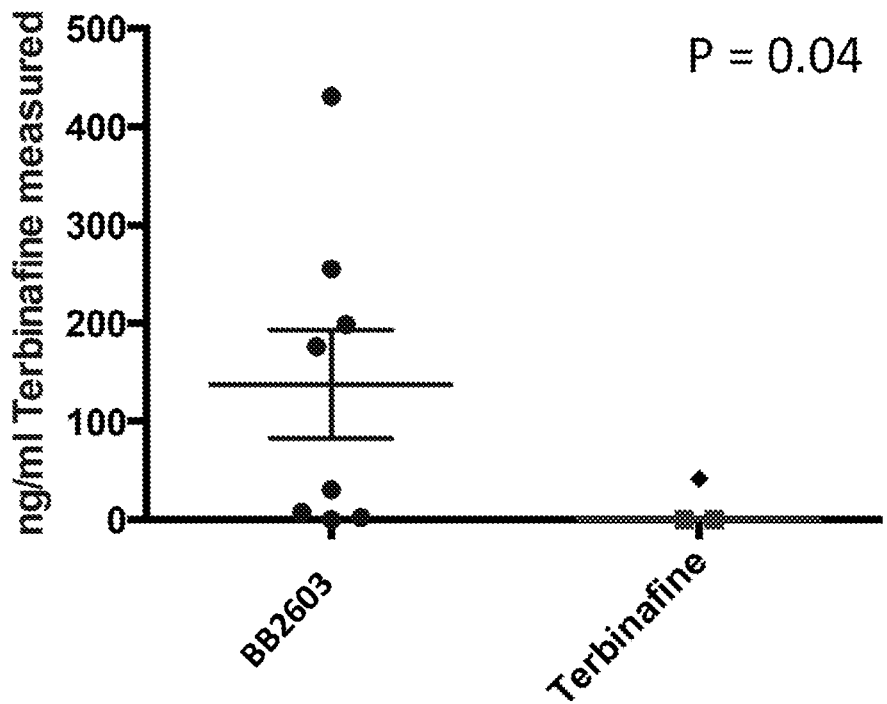
Figure 4:
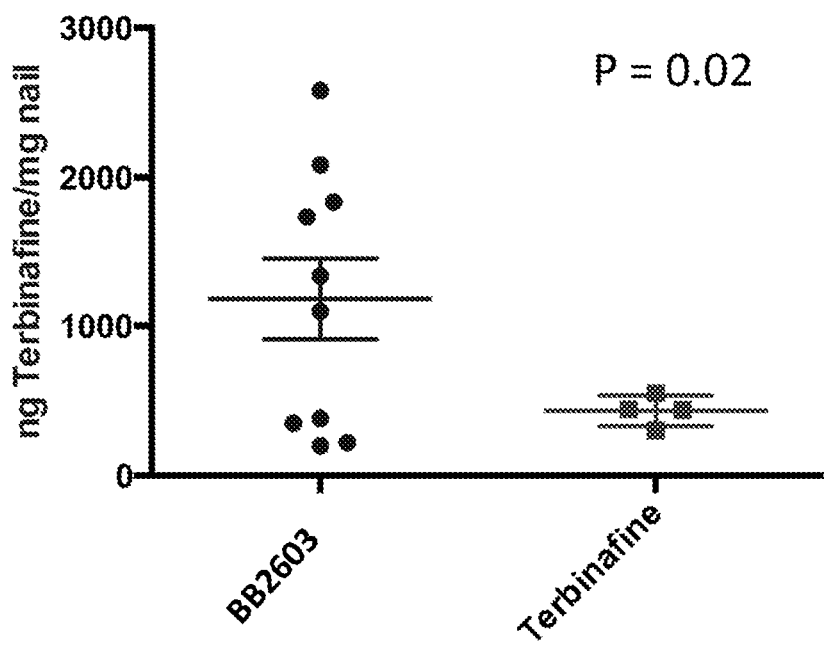
Figure 5:
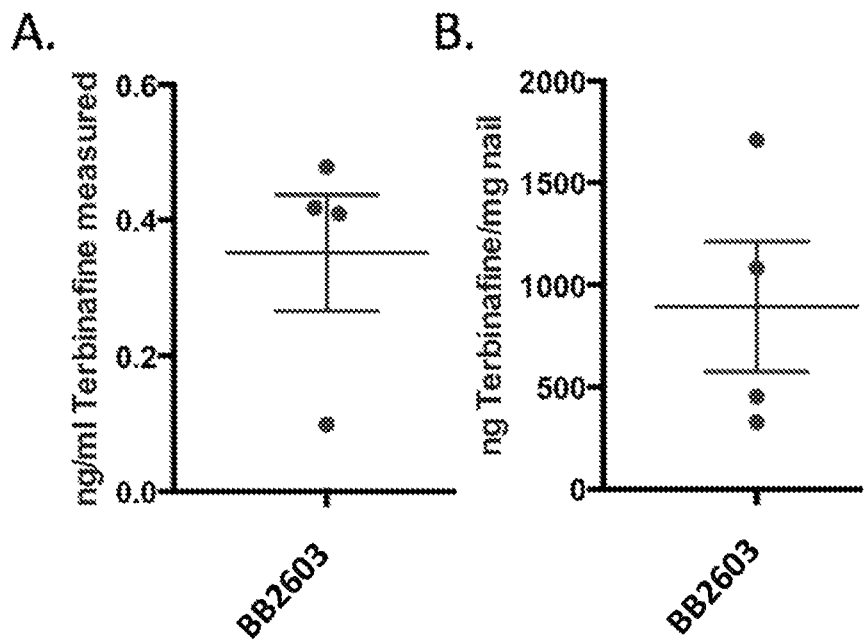
FIG. 5A is a scatter plot graph showing a summary of Franz cell data from multiple dose addition of BB2603 (terbinafine and PHMB nanoparticles) to human nail where the concentration of terbinafine (determined by LC-MS/MS) in ethanol washes from healthy human nails treated with multiple small doses of BB2603 was investigated.
FIG. 5B is a scatter plot graph showing a summary of Franz cell data from multiple dose addition of BB2603 (terbinafine and PHMB nanoparticles) to human nail where the concentration of terbinafine (determined by LC-MS/MS) in dissolved nail samples from healthy human nails treated with multiple small doses of BB2603 was investigated.

As shown in FIGS. 3 and 4, samples treated with BB2603 consistently demonstrated penetration of terbinafine through healthy human nail samples. Terbinafine could be detected both in the collection chamber solution and ethanol washes of the underside of the nail as early as 1 day of incubation. Analysis of the ethanol washes from the underside of nails treated with BB2603 for 7 days demonstrated robust drug delivery by BB2603 through the nail (as shown in FIG. 3). The amount of delivery varied between samples, probably due to natural variation in the nail samples, but in all cases would be predicted to be greater than that required to achieve a mycological killing dose.

In contrast, terbinafine solutions did not penetrate the nail and in all the experiments using an equivalent drug concentration to BB2603 (0.1 mg/ml) the amount of terbinafine passing through the nail was below the limit of detection (<0.1 ng/ml) in the LC-MS/MS (as illustrated in FIG. 3). By assuming that terbinafine had penetrated to a concentration of 0.1 ng/ml a statistical test could be applied to the data to demonstrate that the BB2603 results are significantly different to those of simple terbinafine solutions. The p value of 0.04 calculated in this analysis is an underestimate of significance because the highest possible concentration of terbinafine in the simple terbinafine treated samples was assumed.

The amount of terbinafine in the dissolved nail samples from the Franz cell was also determined at day 7 (as shown in FIG. 4). This represented the amount of drug bound to the top face of the nail (which was not washed off prior to dissolution with 5M NaOH) together with any drug within the nail itself i.e. drug penetrating the nail but not reaching the other side. We saw significantly higher amounts of terbinafine associated with the nails treated with BB2603 compared to terbinafine alone (median difference of approximately 2 fold, p=0.02). This is again consistent with the belief that BB2603 enhances delivery of terbinafine into (and through) the nail.

Multiple Dose Experiments

In the single dose experiments the test solution remains in constant contact with the upper surface of the nail during the entire period of incubation. This does not necessarily reflect the reality of patient application in which the drug would be applied daily to an infected nail and then allowed to dry. Therefore to try and replicate this situation experiments were performed in which 5 μl of BB2603 was added daily to the nail in the Franz cells. This small volume was sufficient to cover the nail discs surface but evaporated prior to the next addition, mimicking more closely a patient applying BB2603 as a daily topical treatment. Samples from the ethanol washes of the nail underside and nail itself were collected and analysed by LC-MS/MS for the presence of terbinafine as described earlier.

In the multiple dose experiments substantial amounts of terbinafine was detected associated with the nails themselves (as illustrated in FIGS. 5A and 5B). This was at a level that was not too dissimilar to that observed in the single dose (constant exposure) experiments with BB2603 (as shown in FIG. 4) and was again higher than the terbinafine controls from the single dose experiment. Significant amounts of terbinafine in the ethanol washes from the undersides of the nail was also detected indicating that the drug had also passed through the nail in this experiment. Compared to the single dose (constant exposure) experiments the levels of drug delivered through the nail were much lower in the multiple dosing experiments. This is consistent with the belief that longer treatment with BB2603, the greater delivery of terbinafine through the nail.

*Trychophyton Mentagrophytes* Anti-Fungal Assay

Earlier experiments had clearly shown that BB2603 delivers terbinafine through the nail but it had to be established that the passage of the drug through the nail would not cause chemical modification leading to a loss of efficacy. An anti-fungal assay using lawns of *T. mentagrophytes* was therefore performed.

*T. mentagrophytes* is a laboratory fungal species relevant to the major pathogens associated with onychomycosis (see for example Wade Foster et al, *J. American Acad. Dermatology*. 2004. 50(5). pp 748-752) and so efficacy against this species would be expected to translate to efficacy against pathogenic *Trychophyton* species such as *T. rubum* (Table 1 below).

TABLE 1

| Fungus | No. strains tested | MIC range (µg/ml) |
|---|---|---|
| *Epidermophyton floccosum* | 42 | 0.001-0.047 |
| *Microsporum* species | 25 | 0.002-0.07 |
| *Microsporum canis* | 49 | 0.006-0.08 |
| *Trichophyton* species | 27 | ≤0.06 |
| *Trichophyton rubrum* | 72 | 0.001-0.038 |
| *Trichophron verrucosum* | 17 | 0.001-0.006 |
| *Trichophron mentagrophytes* | 32 | 0.001-0.006 |
| *Trichophyton interdigitale* | 11 | 0.002-0.028 |
| *Trichophyron terestre* | 1 | 0.002 |

In vitro activity of terbinafine (taken from Leyden, *J. Am. Acad. Dermatol.* 1998. 38: S42-7).

A single colony of *T. mentagrophytes* was picked from a stock plate and grown for 48 hours in 5 mls of YEPD (yeast extract, peptone, dextrose) medium at 30° C. A sterile swab was dipped into the resulting culture and then used to spread a lawn of *T. mentagrophytes* onto a YEPD agar plate supplemented with chloramphenicol (50 ug/ml). Chloramphenicol was included as samples from the Franz cell were not sterile and showed bacterial outgrowth on normal YEPD plates. A 10mm sterile paper disc was soaked in test solution, the excess liquid removed and the disc placed onto the *T. mentagrophytes* lawn. Plates were inverted and incubated at 30° C. for 5 days.

The first experiment performed was to establish the approximate MIC (minimum inhibitor concentration) for terbinafine against *T. mentagrophytes* in a paper disc assay. To do this a 1:10 dilution series of terbinafine.HCl in ddH$_2$O was generated from 60 µg/ml to 0.06 µg/ml. 10 mm sterile paper discs were then soaked in the various dilutions and these placed onto lawns of *T. mentagrophytes*. After 5 days of incubation, zones of clearance were observed around the discs with concentrations of terbinafine having anti-fungal activity against this species (as shown in FIG. 6). The MIC for terbinafine in this assay was 0.6 µg/ml and below this concentration no clear zone of clearance was observed. It was noted that the MIC in this assay is >100× higher than previously reported (6 ng/ml) for terbinafine against *T. mentagrophytes* (with reference to Table 1 above). The reported figures were certainly derived from a liquid MIC assay, which is known to be more sensitive, and so this paper disc assay represented a substantially more stringent test of drug efficacy.

This assay was also used to address the question of whether terbinafine passing through the nail in BB2603 treated samples still retained its antifungal efficacy. To do this a *T. mentagrophytes* lawn assay was performed using a sample of the aqueous phase from one of the Franz cell experiments that quantitative LC-MS/MS analysis demonstrated contained >0.6 µg/ml terbinafine (FIG. 7A-7B). Consistent with the MIC experiment and the quantitative MS results for this sample, a clear zone of clearance with BB2603 could be seen but no effect with the terbinafine control sample. Hence, terbinafine passing through a healthy human nail treated with BB2603 retained its efficacy and was still able to kill *T. mentagrophytes*.

Potential Efficacy of BB2603 in Onychomycosis

The aim with BB2603 was to match the performance of oral terbinafine with a topical formulation of the drug that would not have the safety issues associated with systemic drug exposure. Compared to terbinafine solutions, BB2603 was shown to significantly enhance the delivery of drug through healthy human nail. The key question is whether the amounts achieved by BB2603 dosing would be predicted to be efficacious in the treatment of onychomycosis. To address this question the concentrations of terbinafine observed in the Franz cell experiments were compared to those reported in the nails of patients treated with oral terbinafine (Leyden, *J. Am. Acad. Dermatol.* 1998. 38: S42-7).

Following oral dosing, terbinafine reaches a concentration of 0.1 µg/g in nails after 7 days treatment rising to about 0.25 µg/g after 3 weeks and 0.55 µg/g after 18 months (Leyden, 1998). All of these levels are higher than the MICs of a range of key fungal species associated with onychomycosis (Table 1) and hence explain the drugs efficacy in treating fungal nail infection in these patients.

BB2603 appears to vastly exceed this level in the dissolved nails (FIGS. 4 and 5A-5B), achieving median concentrations equivalent to approximately 1 mg/g of drug in the nail after 7 days (10000 fold higher than oral dosing). However, although lower, terbinafine alone also showed significant levels of drug associated with the dissolved nails (median concentrations of approximately 0.5 mg/g) yet trials with topical terbinafine (at much higher doses than used in these experiments) failed to show efficacy in the treatment of onychomycosis (Elewski et al., *Journal of the European Academy of Dermatology and Venereology.* 2013, 27(3), pp 287-294).

Although substantial amounts of drug are found associated with nails treated with terbinafine solutions, no significant amount of terbinafine was measured to pass through the nail in any of our samples (FIG. 7). So for these samples we concluded that the vast majority of the drug is bound to the upper surface of nail or not penetrating very far into the tissue.

In contrast to terbinafine treated samples, terbinafine was constantly detected on the underside of the nails treated with BB2603 indicating that the drug must have passed into and through the nail. Thus the measurement of terbinafine in the dissolved nails from BB2603 treated samples represents not just drug associated with the upper surface but also drug present throughout the entire depth of the tissue.

It is highly likely that in BB2603 treated nails, an asymmetric distribution of the drug is established, with a larger concentration at the upper (treated) surface and the lowest concentration of drug found towards the bottom of the nail. Because of this, the concentration of terbinafine in the lower portions of the nail was estimated, as this would be the lowest concentration of drug in our samples. To do this it was assumed that the level of drug found on the underside of the nail (in the ethanol washes) was equivalent to the concentration in the nail just above it in the nail disc. Although 3 mm diameter discs of nail were used in the Franz cell experiments, only a 1.5 mm diameter circle of nail is in contact with the solutions in the upper and lower chambers (the rest of the nail forms the seal with the chamber itself). This means that the terbinafine in the ethanol washes of the bottom of the nail is from a surface area of approximately 1.8 mm$^2$ of nail. In order to calculate an approximate concentration in the lower portion of the nail, it was assumed that this portion of the nail to have a depth of 0.1 mm. Overall the nails were about 0.5 mm thick and so this represents about a fifth of the overall nail disc. Thus the volume of the lower portion of the nail disc is 0.18 mm$^3$, equivalent to 0.18 µl. To calculate the concentration in of terbinafine in the lower portion of the nail it was assumed that this volume of nail contained an equivalent amount of terbinafine to that found in the ethanol washes.

The median concentration of terbinafine found on the underside of nails in the multi-dosing experiment was 0.4 ng/ml (FIG. 5A-5B), which is equivalent to 0.04 ng of total terbinafine in the samples. From this, it was estimated that the concentration of terbinafine in the lowest portion of the nail is therefore 220 ng/ml (0.04 ng/0.18 µl). Finally, the density of healthy human nail is 1.34 g/ml (Baraldi et al. 2015, *Pharm. Res.* 32(5), 1626-33) and so the concentration of terbinafine in the lowest portion of the nail is approximately equivalent to 0.165 µg/g (0.22 µg/ml/1.34 g/ml).

From this calculation it can be seen that the multi-dose experiments BB2603 delivered an amount of terbinafine into the lowest portions of the nail that is greater than the concentration of terbinafine reached by oral dosing after 7 days (0.165 µg/g compared to 0.1 µg/g). This level of drug is 2-3 fold higher than that required to kill the least sensitivity fungal species associated with onychomycosis (>0.06 µg/ml, see Table 1). For portions of the nail closer to the treatment surface we would expect the concentration to be much higher. These figures are based on the most conservative data from the multi-dose experiments. For the single dose experiments the median concentration of terbinafine found in the ethanol washes was 185 ng/ml (FIG. 3) and the equivalent predicted nail concentration of drug in the lower portions would be 8 µg/ml, vastly exceeding that achieved by oral dosing and needed for antifungal efficacy.

In summary, 7 days topical application of BB2603 promotes much greater association of terbinafine with healthy human nail than simple terbinafine solutions. Furthermore, BB2603 enables terbinafine to penetrate all the way through the nail indicating that this increase in drug nail levels is due, at least in part, to enhanced drug penetration into the tissue. Even portions of the nail most distal from BB2603 applications are predicted to achieve concentrations of drug that exceed those produced by equivalent oral dosing. This level is greater than the MICs of relevant fungal species and therefore likely to be efficacious in the treatment of onychomycosis.

Oral terbinafine is currently the 'gold standard' for the treatment of onychomycosis and has the highest cure rates with the shortest treatment times (>80% cure following 3-6 months of dosing). However, its use in the treatment of the disease is limited by its safety profile and the fact that terbinafine has significant drug-drug interactions. A large number of these issues are almost certainly due to oral dosing (e.g. liver toxicology, CNS effects) and subsequent high systemic drug exposure. Other topical onychomycosis treatments require long treatment regimes (up to 18 months treatment), have low cure rates (20-40%) and show high rates (>50%) of disease recurrence (Halmy, K. *J. Am. Acad. Dermatol*, 2005. 52(3): 126-126, Scher et al. *J Am Ac Dermatol.* 2007;56(6):939-944). Producing an effective topical formulation of terbinafine is a highly attractive approach to the treatment of onychomycosis because it takes the drug with the best-proven clinical efficacy and removes the safety issues associated with systemic exposure. Achieving this has proven to be challenging and many previous trials with a topical terbinafine solution failed to demonstrate any significant efficacy in the treatment of onychomycosis.

As described above, the amount of terbinafine present in BB2603 for topical application is much lower than would be required for current oral doses. Current systemic treatments would typically employ a daily 250 mg dose of oral terbinafine over 7 days. After 7 days of daily topical application of small volumes of BB2603 to nail samples (mimicking daily patient applications) higher levels of terbinafine in the nail were achieved than reported for oral doses. The drug levels found in the nails are much higher than would be required to show efficacy against all relevant fungal species associated with onychomycosis (Table 1). To give an idea of context, from these experiments the dose of BB2603 that would have been needed to treat an average nail (100 mm$^2$) would have been about 200 µg for a week compared to 1.75 g terbinafine for oral treatment i.e. an 8750 fold lower dose.

Healthy human nails are a much more stringent test of drug penetration. A recent publication by Baraldi et al. (Baraldi et al. 2015), demonstrated that although nails are thicker in onychomycosis, they suffer a significant lose of integrity meaning they are much more permeable to aqueous solutions (3-4 times greater). As such we would expect BB2603 to show even better drug penetration properties in diseased tissue.

Comparison of BB2603 in 20% (v/v) Ethanol Vs. 30% (v/v) Ethanol

All the above experiments employing BB2603 were conducted in solutions of 30% (v/v) ethanol. Initial formulation studies had demonstrated that 30% (v/v) ethanol produced the highest number of BB2603 nanoparticles whilst experiments in solutions of 10% (v/v) ethanol or lower showed a substantial drop-off in particle numbers. Although 30% (v/v) ethanol is an acceptable solution for use in the treatment of topical fungal infections, different % (v/v) ethanol was assessed to see whether lower ethanol content would still maintain efficacy. It was therefore decided to look at formulations of BB2603 in 20% (v/v) ethanol.

Formulations of BB2603 were made as described above, but using 20% (v/v) ethanol instead of 30% (v/v) ethanol. Analyses on the NanoSight LM10 showed no detectable differences in the 20% (v/v) formulations in either the particle numbers or particle distributions of BB2603 compared to 30% (v/v) ethanol. A number of multiple-dose Franz cell experiments with BB2603 formulations in 20% (v/v) ethanol was therefore performed as they best mimicked the type of daily topical dosing a patient would use and were therefore the most meaningful in modeling the efficacy of drug treatment in onychomycosis.

The amount of terbinafine found in the ethanol washes of the undersides of nails treated for a week with daily additions of 5 µl of BB2603 in 20% (v/v) ethanol was analyzed by LC-MS/MS as described in the main text (as illustrated in FIG. 8). These demonstrated a consistent level of terbinafine passing through the nails with a mean value of 0.5 ng/ml in the washes. The data showed a slightly higher trend in the amount of terbinafine passing through the nails treated with BB2603 in 20% (v/v) ethanol suggesting that BB2603 in 20% (v/v) was more effective at delivering drug through the nail. Consistent with this, the amount of terbinafine in the dissolved nails treated with BB2603 in 20% (v/v) ethanol was three-fold higher that those treated with BB2603 in 30% (v/v) ethanol (as shown in FIG. 9).

Taken together, these results demonstrated that using formulations of BB2603 in 20% (v/v) ethanol enhances further the delivery of terbinafine into and through the human nail in Franz cell multiple-dose (daily addition) experiments. Substantially higher amounts of drug are found associated with the nail and the amount of terbinafine passing through the nail is also higher. Calculations show that the median amount of drug in the lower portions of the nail treated with this formulation of BB2603 would be 0.21 µg/g, which is twice that achieved in nails following oral dosing at 7 days and well above that required to kill relevant fungal species in onychomycosis. This result is consistent with the observations of Baraldi et al. (Baraldi et al. 2015) that compounds in aqueous solution have higher levels of penetrance into both healthy and diseased nails compared to those in a 50% (v/v) ethanol solution.

In summary, reducing the ethanol concentration in solutions of BB2603 from 30% to 20% (v/v) has no detectable impact on nanoparticle formation, but interestingly, formulations of BB2603 in 20% (v/v) ethanol demonstrate improved terbinafine delivery properties both into and through healthy human nail in Franz cell experiments mimicking the daily application of drug in the treatment of onychomycosis.

Formulations of Onychomycosis Medicaments

It is envisaged that in-light of the above experiments, the following formulation would be effective as a topical medicament for onychomycosis:

| Formula A | |
| --- | --- |
| Ingredient | Amount |
| Terbinafine•HCl | 100 µg/ml |
| PHMB | 300 µg/ml |
| Ethanol | 20% (v/v) |
| Distilled water | ≥80% (v/v) |

Other formulations may also provide effective topical medicaments:

| Formula B | |
| --- | --- |
| Ingredient | Amount |
| Terbinafine•HCl | 100 µg/ml |
| PHMB | 300 µg/ml |
| Ethanol | 30% (v/v) |
| Distilled water | ≥70% (v/v) |

| Formula C | |
| --- | --- |
| Ingredient | Amount |
| Terbinafine•HCl | 50 µg/ml |
| PHMB | 150 µg/ml |
| Ethanol | 20% (v/v) |
| Distilled water | ≥80% (v/v) |

| Formula D | |
| --- | --- |
| Ingredient | Amount |
| Terbinafine•HCl | 200 µg/ml |
| PHMB | 600 µg/ml |
| Ethanol | 20% (v/v) |
| Distilled water | ≥80% (v/v) |

| Formula E | |
| --- | --- |
| Ingredient | Amount |
| Terbinafine•HCl | 150 µg/ml |
| PHMB | 450 µg/ml |
| Ethanol | 30% (v/v) |
| Distilled water | ≥70% (v/v) |

A formulation in accordance with the present invention was prepared according to Formula F below and denoted BB2603.

| Formula F | |
| --- | --- |
| Ingredient | Amount (% w/w) |
| Terbinafine•HCl | 0.1 |
| PHMB | 0.3 |
| Ethanol | 20 |
| Distilled water | 79.6 |

The formulation of Formula F was placed in a spray bottle. Trials were then conducted by periodically spraying, over a 1-2 week period, the formulation on the toes of patients suffering from onychomycosis (and additionally tinea pedis in some cases). The treatments proved successful and successfully and quickly treated patients suffering from onychomycosis (and tinea pedis), without subsequent relapse.

Dosage Regime

Experiments were conducted to identify an optimum spray distance from the foot to give complete coverage of the toes and inter-digital spaces. A formulation in accordance with the present invention was prepared according to Formula F (BB2603) as detailed above.

The total topical dose a patient was likely to receive following spray application of BB2603 was estimated. It was presumed that a patient would apply 5 pumps of the spray per treatment. Each pump delivers 100 µl of BB2603 and so the total application from 5 pumps is 500 µl.

Basic spray characteristics of the pump were assessed using a solution of blue food colouring. 400 µl of blue food colouring was diluted into 20 ml of 20% v/v ethanol and transferred into a clean spray bottle. The spray was primed by pumping it 5 times in order to remove any air from the spray nozzle. The dye spray was then sprayed once onto a sheet of white paper in order to form a dye spot. Spraying was performed at 5, 10, 15, 20 and 25 cm distance from the paper and this resulted in a range of spots of different diameters (FIGS. 10A-E).

As can be seen from FIGS. 10A-E each spot has essentially three zones. In the centre there is a zone with heavy dye loading, surrounding this is a zone of 100% dye coverage (no visible white paper) and outside this is a more diffuse zone of dye coverage.

Ideally topical treatment with BB2603 needs to achieve 100% coverage of the infected area and surrounding tissues (toes and inter-digital spaces) in order to ensure that any non-visible fungal infection of either the toenail or proximal skin is treated with the drug. Because of this, the major consideration in optimizing the spray distance for treatment is the diameter of the zone of 100% coverage. To analyse each spot, the diameter of the zone of 100% coverage was measured together with the diameter of the total spot (edge of visible dye). These were plotted on a graph against the distance of the spray from the paper, as shown in FIG. 15. This demonstrated an approximately linear relationship between the width of the overall spot and the spray distance (FIG. 11). However, the area of 100% dye coverage reduced when the spray distance was greater than 15 cm.

Based on the spot tests a spray distance of between 5-15 cm resulted in the greatest diameter of the zone of 100% coverage. When the distance was more than 15 cm, although the total area of visible dye increased, the area of 100% coverage from a single application decreased (FIG. 11).

The effect of multiple applications on the area of dye coverage was assessed by spraying the paper 5 times from a distance of 10 cm (FIG. 12). This demonstrated an increase in 100% dye coverage to a spot with a diameter of 10 cm and an area of approximately 78 cm². Assuming a foot width (across the toes) of 10 cm this should be sufficient to cover an area more than 7 cm down from the tip of the toe, which is more than sufficient to cover the toes and inter-digital spaces.

Thus spray distances of between 5-15 cm would appear to be optimal for patient treatment with BB2603 from this spray device.

Foot Template Experiments

From the spray tests the optimum distance for spray application of BB2603 from the spray bottles is between 5-15 cm. The multiple-application test (FIG. 12) indicated that this should be sufficient to provide 100% drug coverage across the toe, inter-digital spaces and forefoot of a patient based on the area of the spot. To confirm this and to calculate the approximate total dose a patient would receive a series of experiments using foot templates were conducted.

A foot template was constructed from paper by drawing around a volunteer's foot (male, UK size 10). The paper template was cut out and then laid on top of a blank sheet of paper. Dye was sprayed five times from a distance of 10 cm over the front of the paper "foot" and ensuring all the "toes" were treated. Dye was found on both the foot template and underlying paper (FIGS. 13A and 13B). After the dye had dried, areas of 100% dye coverage from both the foot and the underlying paper were drawn around, cut out and weighed. The percentage of drug dose on the "foot" was calculated as follows:

$$\% \text{ dose} = \frac{\text{weight of foot template}}{\text{weight of foot template} + \text{weight of underlying paper}} \times 100$$

Visually it was clear that five sprays from a distance of 10 cm were sufficient to give 100% coverage across the entire foot template. By weighing the areas of 100% dye coverage it was possible to compare the approximate areas of coverage and estimate the proportion of the dose received topically on the foot. The data is summarised in table 2:

TABLE 2

Weight of foot template and overspill with 100% spray coverage and proportion of 100% spray area made up by foot template

| Foot template 100% coverage (mg) | Overspill 100% coverage (mg) | Total 100% coverage (mg) | Percentage on foot template |
|---|---|---|---|
| 449 | 381 | 830 | 54.1 |
| 510 | 460 | 970 | 52.6 |
| 452 | 422 | 874 | 51.7 |

TABLE 2-continued

Weight of foot template and overspill with 100% spray coverage and proportion of 100% spray area made up by foot template

| | Foot template 100% coverage (mg) | Overspill 100% coverage (mg) | Total 100% coverage (mg) | Percentage on foot template |
|---|---|---|---|---|
| Average | 470 | 421 | 891 | 52.8 |
| Stnd Dev | 34 | 40 | 72 | 1.2 |

Based on this experiment, it was estimated that a patient spraying their foot with BB2603 from a spray distance of 10 cm would receive about 50% of the total application topically.

In summary, these experiments indicate that spray treatment of BB2603 using five "pumps" from the spray bottles at a distance of between 5-15 cm should be sufficient to give 100% coverage of the toes, inter-digital spaces and front of the foot. From the foot template experiments it is estimated that such application would result in a patient receiving a topical dose of about 50% of that sprayed. For five "pumps" this would be equivalent to a topical dose of 250 µl or a total dose of 25 µg of terbinafine.

The forgoing embodiments are not intended to limit the scope of the protection afforded by the claims, but rather to describe examples of how the invention may be put into practice.

The invention claimed is:
1. A composition comprising:
   (a) terbinafine, or salt thereof, present in an amount in the range of about 0.005% w/w to about 1% w/w;
   (b) a polymer capable of forming nanoparticles, wherein the nanoparticles are formed with and/or in the presence of terbinafine, or salt thereof, wherein the polymer is present in an amount in the range of about 0.015% w/w to about 3% w/w, and wherein the polymer comprises a linear and/or branched or cyclic polymonoguanide/polyguanidine or polybiguanide;
   (c) alcohol at less than 30% w/w; and
   (d) water at up to about 90% w/w.
2. The composition according to claim 1, wherein the composition comprises:
   (a) terbinafine, or derivative or salt thereof, present in an amount in the range of about 0.025% w/w to about 0.2% w/w;
   (b) polymer present in an amount in the range of about 0.75% w/w to about 0.6% w/w;
   (c) alcohol present in an amount in the range of about 20% w/w to about 29% w/w; and
   (d) water present in an amount in the range of about 70% w/w about 90% w/w.
3. The composition according to claim 2, wherein the composition comprises:
   (a) terbinafine, or salt thereof, at about 0.1% w/w;
   (b) polymer at about 0.3% w/w;
   (c) alcohol at about 20% w/w; and
   (d) water at up to about 79.6% w/w.
4. The composition according to claim 1, wherein the polymer comprises polyhexamethylene biguanide (PHMB).
5. The composition according to claim 3, wherein the alcohol comprises ethanol.
6. The composition according to claim 1, wherein the composition further comprises one or more of the following components: buffers, excipients, binders, oils, water, emulsifiers, glycerine, antioxidants, preservatives, fragrances and urea.

7. A liquid dispensing device comprising a vessel containing the composition of claim 1, a nozzle for expelling the composition from the vessel, and a pump action mechanism operable by the user to draw a pre-defined quantity of the composition from the vessel and expel it via the nozzle, thereby atomizing the composition on a user's toes and/or inter-digital spaces and/or front of the foot.

8. The device according to claim 7, wherein the device further comprises a metering valve, through which the pre-defined quantity of composition is dispensed.

9. The device according to claim 7, wherein the device further comprises and/or is associated with a distance indicator to indicate the correct distance the user should place the nozzle of the device relative to the infected area.

10. A method of treating onychomycosis and/or tinea pedis, the method comprising administering the composition of claim 1 topically to provide to an infected area a daily dose of terbinafine in the range of about 5 µg to about 50 µg.

11. The method according to claim 10, wherein the daily dose provided to the infected area is about 25 µg of terbinafine.

12. The method according to claim 10, wherein the composition is administered by a liquid dispensing device, the device comprising: a vessel containing the composition, a nozzle for expelling the composition from the vessel, and a pump action mechanism operable by the user to draw a pre-defined quantity of the composition from the vessel and expel it via the nozzle, thereby atomizing the composition on a user's toes and/or inter-digital spaces and/or front of the foot.

13. The method according to claim 12, wherein in use, when the nozzle of the device is placed in the range of about 5 cm to 15 cm of the infected area and the nozzle of the device can dispense all of the required dose with up to about 5 pumps.

14. The method according to claim 12, wherein the device further comprises a metering valve, through which the pre-defined quantity of composition is dispensed.

15. The method according to claim 12, wherein the pre-defined quantity of composition comprises up to about 200 µl.

16. The method according to claim 12, wherein the composition is administered by means of a spray application.

17. The method according to claim 16, wherein the daily dose is administered using one or more spray applications.

18. The method according to claim 16, wherein the spray is effective to cover the digits and/or the inter-digital spaces and/or front of the foot or hand.

* * * * *